US011234465B2

(12) United States Patent
Skoda

(10) Patent No.: US 11,234,465 B2
(45) Date of Patent: Feb. 1, 2022

(54) HEATING MECHANISMS FOR VAPORIZERS

(71) Applicant: Ahkeo Labs, LLC, Mayfield Village, OH (US)

(72) Inventor: Brent M. Skoda, Irving, TX (US)

(73) Assignee: Ahkeo Labs, LLC, Mayfield Village, OH (US)

(*) Notice: Subject to any disclaimer, the term of this patent is extended or adjusted under 35 U.S.C. 154(b) by 177 days.

(21) Appl. No.: 15/885,012

(22) Filed: Jan. 31, 2018

(65) Prior Publication Data
US 2019/0231992 A1 Aug. 1, 2019

Related U.S. Application Data

(60) Provisional application No. 62/452,913, filed on Jan. 31, 2017.

(51) Int. Cl.
*A24F 40/65* (2020.01)
*A61M 11/04* (2006.01)
(Continued)

(52) U.S. Cl.
CPC ............ *A24F 40/65* (2020.01); *A61M 11/042* (2014.02); *A24F 40/10* (2020.01); *A61M 15/002* (2014.02);
(Continued)

(58) Field of Classification Search
CPC .......... A61M 15/06; A61M 2205/3553; A61M 2205/3592; A61M 15/0003; A61M 2205/3368; A61M 2205/609; A61M 15/002; A61M 15/0021; A61M 15/0065; A61M 15/0066; A61M 15/008; A61M 15/02; A61M 2205/0211; A61M 2205/3303; A61M 2205/3317; A61M 2205/3331; A61M 2205/3334; A61M 2205/3561; A61M 2205/3569; A61M 2205/3584; A61M 2205/3606; A61M 2205/362; A61M 2205/364; A61M 2205/3653; A61M 2205/366; A61M 2205/3673; A61M 2205/50; A61M 2205/502; A61M 2205/505;
(Continued)

(56) References Cited

U.S. PATENT DOCUMENTS

2013/0199528 A1* 8/2013 Goodman ......... A61M 16/1075
128/203.26
2013/0298905 A1* 11/2013 Levin ..................... A24F 40/00
128/202.21
(Continued)

*Primary Examiner* — Ibrahime A Abraham
*Assistant Examiner* — Chris Q Liu
(74) *Attorney, Agent, or Firm* — Foley & Lardner LLP

(57) ABSTRACT

At least one aspect is directed to a system and method for modifying the operational settings of vaporizer devices. An application executed on a client device may render a graphical user interface on a display of the client device for inputting operational settings of a vaporizer device. Once inputted via the user interface of the application, the client device may transmit the operational settings via a network to the vaporizer device. In response to the receipt, the vaporizer device may store and save the operational settings and may adjust the operations of one or more components of the vaporizer device to satisfy the operational settings.

14 Claims, 13 Drawing Sheets

(51) Int. Cl.
  *A61M 15/06* (2006.01)
  *A24F 40/10* (2020.01)
  *A61M 15/00* (2006.01)
(52) U.S. Cl.
  CPC ..... *A61M 15/06* (2013.01); *A61M 2205/0211* (2013.01); *A61M 2205/3331* (2013.01); *A61M 2205/3368* (2013.01); *A61M 2205/3553* (2013.01); *A61M 2205/3561* (2013.01); *A61M 2205/52* (2013.01); *A61M 2205/583* (2013.01)
(58) Field of Classification Search
  CPC ........ A61M 2205/52; A61M 2205/583; A61M 2205/584; A61M 2205/6009; A61M 2205/6018; A61M 2205/702; A61M 2205/7518; A61M 2205/7545; A61M 2205/8206
  USPC ................................................ 392/404, 386
  See application file for complete search history.

(56) References Cited

U.S. PATENT DOCUMENTS

| | | | |
|---|---|---|---|
| 2015/0320116 A1* | 11/2015 | Bleloch | H05B 6/108 219/628 |
| 2016/0106936 A1* | 4/2016 | Kimmel | A24F 40/51 128/202.21 |
| 2016/0198771 A1* | 7/2016 | Goggin | A24F 40/50 131/329 |
| 2016/0331034 A1* | 11/2016 | Cameron | A24F 47/008 |
| 2017/0014582 A1* | 1/2017 | Skoda | A61M 15/06 |
| 2017/0181468 A1* | 6/2017 | Bowen | A24F 42/10 |
| 2017/0188626 A1* | 7/2017 | Davis | A24F 40/40 |
| 2017/0208864 A1* | 7/2017 | Anderson, Jr. | H05B 1/0244 |
| 2017/0280775 A1* | 10/2017 | Manca | B05B 7/2464 |
| 2017/0280777 A1* | 10/2017 | Manca | H05B 1/0244 |
| 2017/0354186 A1* | 12/2017 | Johnson | H04R 1/028 |
| 2018/0020723 A1* | 1/2018 | Davis | B65D 83/72 392/404 |

* cited by examiner

HEATING MECHANISMS FOR VAPORIZERS

RELATED APPLICATIONS

The present application claims the benefit of and priority to U.S. Provisional Application No. 62/452,913, titled "IMPROVED HEATING MECHANISMS FOR VAPORIZERS" and filed Jan. 31, 2017, the entire content of which is hereby incorporated by reference.

TECHNICAL FIELD

The present application relates generally to apparatuses and systems for operating vaporizers and inhalers.

BACKGROUND

Vaporizers or inhalers may be used to administer, transform or otherwise dispense a substance in a consumable format (i.e. vapor, fine powder, mist, liquid) for the user. One form of vaporizers includes electronic cigarettes. The substance for consumption through a vaporizer or vaporization apparatus or device may include caffeine, an energy boosting formulation, a flavored substance, a medicinal formula, a supplement, a vitamin, a mineral, any ingredient, or various other products for consumption alone or in combination. Vaporizers configured for consumption by a user via inhaling may be operated through the use of various electronic components configured to heat the substance, which substance may be stored as a liquid, to transform the liquid substance into a vapor phase and present the substance for consumption to the user via an outlet port configured to permit inhaling of the substance. Current vaporizers, however, may be prone to burning (as opposed to vaporizing) the substance, thereby rendering the substance unsuitable or undesirable for consumption.

SUMMARY

Various embodiments disclosed herein provide apparatuses, systems, and methods related to the operation of a device configured to convert substances into a form configured for consumption by inhalation.

Substances for consumption may be inserted or placed into a chamber of a vaporizer or a vaporization apparatus or device. These substances may include caffeine, an energy boosting formulation, a flavored substance, a medicinal formula, a supplement, a vitamin, a mineral, any ingredient, or various other products for consumption alone or in combination. At present, vaporizers may be prone to combusting the substance yielding various oxides, thereby rendering the substance unsuitable or undesirable for consumption. Using a ceramic chamber or oven may yield in an even application of heat over the substance, thereby reducing the likelihood that the substance to be consumed will undergo combustion.

At least one aspect is directed to a system and method for modifying the operational settings of vaporizer devices. An application executed on a client device may render a graphical user interface on a display of the client device for inputting operational settings of a vaporizer device. The operational settings may include: an amount of electrical energy provided by a power source to a heating element of the vaporizer device; a duration of time of the electrical energy provided by the power source to the heating element; an amount of thermal energy applied on substances of a liquid cartridge by the heating element; a duration of time of the thermal energy applied on the substances of the liquid cartridge by the heating element; an amount of liquid to release from the liquid cartridge for heating by the heating element; a rate of liquid to release from the liquid cartridge for heating by the heating element; and a time duration liquid to release from the liquid cartridge for heating by the heating element, among others. Once inputted via the user interface of the application, the client device may transmit the operational settings via a network to the vaporizer device. In response to the receipt, the vaporizer device may store and save the operational settings and may adjust the operations of one or more components of the vaporizer device to satisfy the operational settings.

At least one other aspect is directed to an apparatus for heating a liquid substance for inhaled consumption. A vaporizer device may include a heating mechanism, a liquid cartridge, and a ceramic chamber. The heating mechanism may be thermally coupled to the ceramic chamber to convert electrical energy to thermal energy for heating the liquid cartridge. The liquid cartridge may hold a substance for consumption in liquid form. An inlet of the liquid cartridge may be inserted into the ceramic chamber. The inlet of the liquid cartridge may release the substance in liquid form into the ceramic chamber. While in the ceramic chamber, the substance may undergo flash or partial evaporation from the heat provided by the heating mechanism converting from liquid to gaseous form. The ceramic chamber may include an outlet to an output pipe for exiting the substance in vapor form for consumption by the user of the vaporizer device.

At least one other aspect is directed to an apparatus for heating a liquid substance for inhaled consumption. A vaporizer device may include a heating mechanism, a liquid cartridge, and a ceramic chamber. The heating mechanism may be thermally coupled to the ceramic chamber to convert electrical energy to thermal energy for heating the liquid cartridge. The liquid cartridge may hold a substance for consumption in liquid form. The liquid cartridge may include an outlet for to an output pipe for exiting the substance in vapor form for consumption by the user of the vaporizer device. The thermal energy applied to the substance of the liquid cartridge by the heating mechanism through the ceramic chamber may convert the substance from liquid to gaseous form. The substance in gaseous form may exit the liquid cartridge via the outlet.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

It should be understood that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

The features and advantages of the concepts disclosed herein will become more apparent from the detailed description set forth below when taken in conjunction with the drawings.

DETAILED DESCRIPTION

Following below are more detailed descriptions of various concepts related to, and embodiments of, inventive variable counterweight systems and methods of operating variable counterweight systems. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Section A describes embodiments of improved heating mechanisms for vaporizers.

Section B describes a network environment and computing environment which may be useful for practicing various computing related embodiments described herein.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

A. Heating Mechanisms for Vaporization and Inhaler Apparatus

Substances for consumption may be inserted or placed into a chamber of a vaporizer or a vaporization apparatus or device. These substances may include caffeine, an energy boosting formulation, marijuana, a flavored substance, a medicinal formula, a supplement, a vitamin, a mineral, any ingredient, or various other products for consumption alone or in combination. At present, vaporizers may be prone to combusting the substance yielding various oxides, thereby rendering the substance unsuitable or undesirable for consumption. Using a ceramic chamber or oven may provide an even application of heat over the substance, thereby reducing the likelihood that the substance to be consumed will undergo combustion or be burnt.

Figure 1:
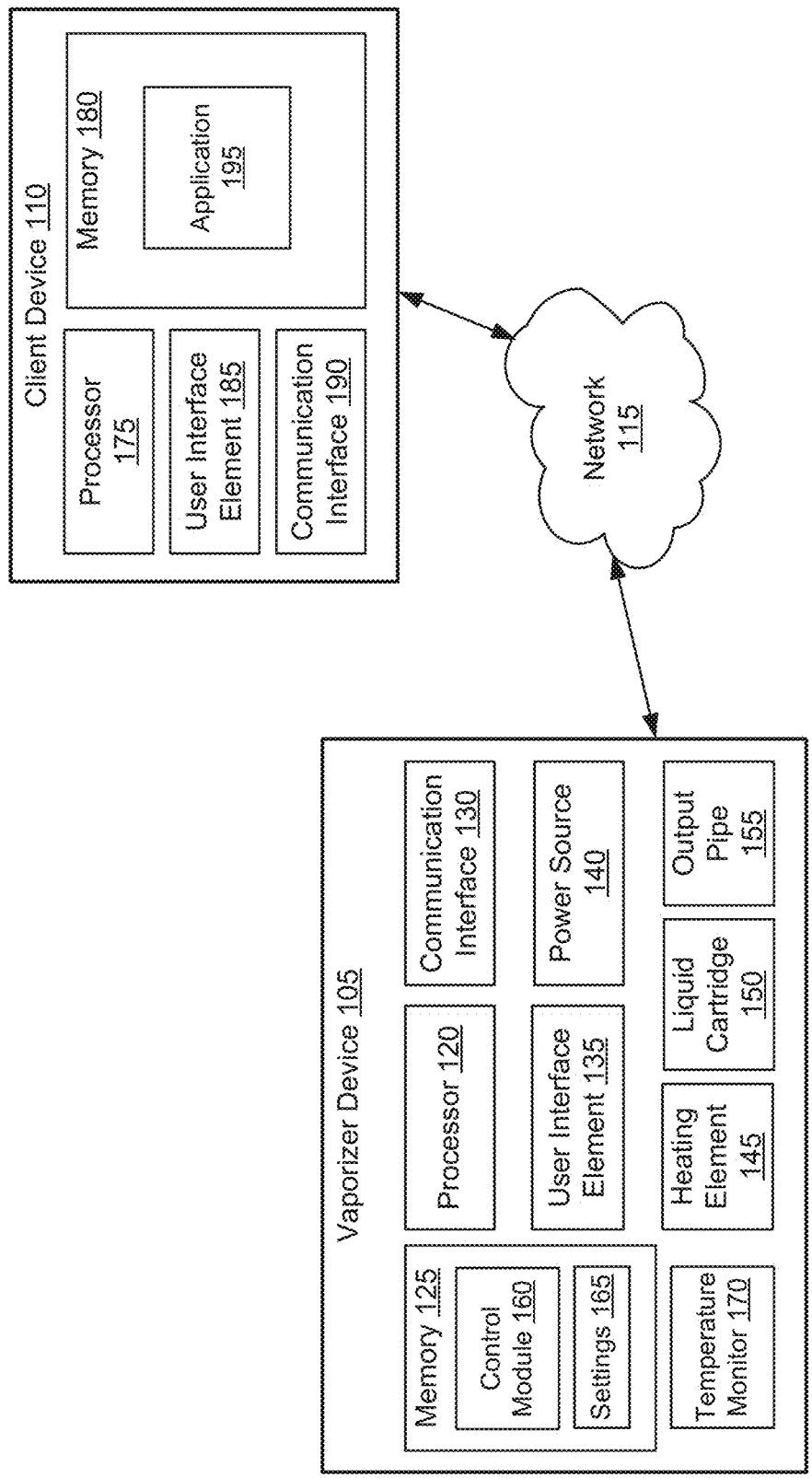
FIG. 1 is a block diagram depicting a communication network environment for a vaporization and inhaler apparatus, according to an illustrative embodiment.

Referring first to FIG. 1, FIG. 1 depicts a communication network environment 100 for a vaporization and inhaler apparatus. In overview, the environment 100 may include a mobile vaporizer device 105 and a client device 110 communicatively coupled via a network 115. The vaporizer device 105 and the client device 100 may each include the components and functionalities of the computing system 400 detailed herein in conjunction with FIGS. 4A-4D. The network may include the functionalities of the network 404 and the cloud 408 detailed herein in conjunction with FIGS. 4A-4D.

The vaporizer device 105 may be used by the user to inhale and consume substances vaporized therein. The vaporizer device 105 may include a processor 120, memory 125, a communication interface 130, a user interface element 135, a power source 140, a heating element 145, a liquid cartridge 150, an output pipe 155. The processor 120 may include the functionalities of the main processor 420 or the CPU 421 detailed herein in conjunction with FIGS. 4C and 4D. The memory 125 may include the functionalities of the main memory 428, and cache memory 440 detailed herein in conjunction with FIGS. 4C and 4D, and may include computer-readable instructions or other data (e.g., a control module 160 and settings 165) to be processed and executed by the processor 120. The communication interface 130 may include the functionalities of the network interface 418 detailed herein in conjunction with FIGS. 4C and 4D. The user interface element 135 may include the functionalities of the I/O control 423, display devices 424a-n, keyboard 426, pointing device 427, I/O devices 430a-n detailed herein in conjunction with FIGS. 4C and 4D.

To provide the substance in vaporous form for consumption by the user, the power source 140 may provide electricity to the heating element 145. In some embodiments, the power source 140 may include a battery. The power source 140 may also include a recharger for the battery. The recharger may include a USB plug-in. The power source 140 may include an inductive charger. In some embodiments, the power source 140 may include a turbine converting air blown in by the user or operator of the vaporizer device 105 to electrical energy. In some embodiments, the power source 140 may include a crank or shaft mechanism to convert mechanical energy (e.g., turn of the handle by the user) exerted by the user onto the vaporizer device 105 to electrical energy. In some embodiments, the power source 140 may include a plug coupled to another power source (e.g., via an electrical power outlet). In some embodiments, the power source 140 may include a photovoltaic cell to convert solar energy into the electrical power. The power source 140 may include any number of sources to provide electrical energy to the components of the vaporizer device 105.

The electricity from the power source 140 may in turn be converted into thermal energy by the heating element 145. In some embodiments, the heating element 145 may include a metallic coil, ribbon, or straight wire of a specific resistance. The metallic substance of the heating element 145 may include iron-chromium-aluminum (FeCrAl), copper-nickel (CuNi), nickel-chromium (NiCo), and various metallic alloys, among others. In some embodiments, the heating element 145 include a ceramic element, such as molybdenum silicide (MoSi2) or silicon nitride (Si3N4), silicon carbide (SiC), among others. In some embodiments, the heating element 145 may include a polymer heating element, such as conductive rubber. In some embodiments, the heating element 145 may include a composite material element. In some embodiments, the electrical resistance of the heating element 145 may be adjustable. In some embodiments, the electrical resistance of the heating element 145 may be prefixed. In some embodiments, the heating element 145 may include two-part heating with a first component and a second component. The second component may include ceramic material, and may be in the form of a chamber, oven, or encasing. The first component may have a higher thermal conductivity than the second component. The first component may be metallic, semi-metallic, ceramic, or any other material with higher thermal conductivity than the second component. The first component may be used to heat the second component at a faster rate, thereby reducing initialization time to heat the substance. The heating element 145 may include any number of devices or apparatuses to convert electrical energy into the thermal energy to apply to the liquid cartridge 150 via a ceramic chamber, oven, or encasing.

Advantageously, heating the liquid cartridge 150 via the ceramic chamber may allow for a slower application and more event distribution of the heat onto the substance. Furthermore, as the ceramic chamber has lower thermal conductivity than other materials (e.g., metal or glass) thereby resulting in a slower burn, the application of thermal heat to the substance in liquid may reduce the likelihood of combustion. The slower burn and more evenly distributed heat may also increase the likelihood that the oil, for example, cannabis oil, in the liquid cartridge 150 to convert from liquid form to gaseous form without loss or combustion of the compounds therein (e.g., tetrahydrocannabinol, tetrahydrocannabinolate, monoterpenes, sesquiterpene, etc.). In this manner, the user of the vaporization device 105 may inhale a greater percentage of the substance originally contained in the liquid cartridge 150. Furthermore, having a lower thermal conductivity may also allow the ceramic chamber to better withstand higher temperatures and thermal energy applied by the heating element 145. In addition, using ceramic as the material for the encasing may prevent the substance from sticking or coalescing on the inner surfaces of the ceramic chamber, thereby further reducing potential loss of substance originally in the liquid cartridge 150.

The thermal energy radiating from the heating element 145 may be applied to the liquid cartridge 150. The liquid cartridge 150 may include or may house substances in liquid form for consumption by the user. The liquid cartridge 150 may be 1 cm to 8 cm in length, 3 mm to 40 mm in height, and 3 mm to 55 mm in width. The liquid cartridge 150 may be detachable from the vaporizer device 105, so as to allow the user to replace or change one liquid cartridge with another liquid cartridge. In some embodiments, the liquid cartridge 150 may include an inlet into a ceramic chamber, oven, or encasing for inserting, flowing, or dripping the substance heated by the heating element 145 for vaporization. In some embodiments, the liquid cartridge 150 may include a button (mechanical or mechno-electrical) to allow dripping of the substance into the ceramic chamber, oven, or encasing heated by the heating element 145. In some embodiments, the liquid cartridge 150 may include an outlet connected to the output pipe 155 for consumption of the substance in vaporous form to the user. In some embodiments, the liquid cartridge 150 may include an opening to refill the substance in liquid form therein. In some embodiments, the user interface element 135 may be used to control dripping or flowing of the substance from the liquid cartridge 150 to the ceramic chamber heated by the heating element 145. The liquid cartridge 150 may be made of metallic, semi-metallic, ceramic, or other materials. In some embodiments, the liquid cartridge 150 may have a lower thermal conductivity than the ceramic chamber thermally coupled to the heating element to prevent combustion of the substance in liquid form while inside the liquid cartridge 150.

Once the substance in liquid form from the liquid cartridge is vaporized, the output pipe 155 may provide the substance in vaporous form to the user. The output pipe 155 may include a conduit, vent, mouthpiece, outlet, or channel for providing the substance in vaporous form to the user. In some embodiments, the output pipe 155 may be a part of the liquid cartridge 150. In some embodiments, the output pipe 155 may be a separate portion of the vaporization device 105.

The control module 160 may be executed by the processor 120 to control and regulate the vaporization of the substance initially in the liquid cartridge 150. In some embodiments, the control module 160 may set, change, or adjust the electrical energy provided by the power source 140 to the heating element 145, thereby changing the thermal energy provided by the heating element 145 to the substances of the liquid cartridge 150. In some embodiments, the control module 160 may set, change, or adjust the thermal energy or temperature provided by the heating element 145. In some embodiments, the control module 160 may set, change, or adjust the amount of substance from the liquid cartridge 150 dripping into the ceramic chamber, oven, or encasing heated by the heating element 145.

In some embodiments, the control module 160 may set, change, or adjust the electrical energy provided by the power source 140 or the thermal energy applied by the heating element 145 in accordance with the settings 165. The settings 165 may be transmitted or provided by the application 195 executed on the client device 110 via the network 115. In some embodiments, the settings 165 may specify the amount of electrical energy and time at which to provide the electrical energy from the power source 140 to the heating element 145. In some embodiments, the settings 165 may specify the amount of thermal energy, the temperature, and the time at which to provide the thermal energy from the heating element 145 to the ceramic chamber housing the liquid cartridge 150. In some embodiments, the settings 165 may specify the amount and the rate of the substance in liquid form from the liquid cartridge 150 is to be released (e.g., dripping or flowing) to the ceramic chamber housing heated by the heating element 145. In some embodiments, the settings 165 may specify the amount and the rate of substance in gaseous form is to exit the output pipe 155 for consumption by the user of the vaporization device 105.

In some embodiments, the control module 160 may read or use the data from the temperature monitor 170 to set or adjust the functionalities of the power source 140, the heating element 145, the liquid cartridge 150, and other components of the vaporizer device 105. By comparing the temperature readings to a predefined window, the control module 160 may set or adjust the one or more components of the vaporizer device 105 to allow for desired operations.

In some embodiments, temperature monitor 170 may measure the temperature of the power source 140. The control module 160 may compare the measured temperature of the power source 140 to a predefined window of temperatures. If the temperature is greater than the predefined window, the control module 160 may decrease electrical energy from the power source 140 (e.g., lower electrical current) or shut off the power source 140 (e.g., by opening a mechanical switch). If the temperature is less than the predefined window, the control module 160 may increase the power provided by the power source 140 (e.g., higher electrical current).

In some embodiments, the temperature monitor 170 may measure the temperature of the heating element 145. The control module 160 may compare the measured temperature of the heating element 145 to a predefined window of temperatures. If the temperature is greater than the predefined window, the control module 160 may decrease thermal energy from the heating element 145 or shut off the heating element 145 (e.g., disconnect from the power source 140). If the temperature is less than the predefined window, the control module 160 may increase the thermal power provided by the heating element 145 (e.g., increase electrical power from power source 140 or increase resistance of the heating element 145).

In some embodiments, the temperature monitor 170 may measure the temperature of the liquid cartridge 150. The control module 160 may compare the measured temperature of the liquid cartridge 150 to a predefined window of temperatures. If the temperature is greater than the predefined window, the control module 160 may decrease thermal energy from the heating element 145, shut off the heating element 145, decrease electrical energy from the power source 140, or shut off the power source 140. If the temperature is less than the predefined window, the control module 160 may increase the thermal power provided by the heating element 145 or electrical power provided by the power source 140.

In the context of environment 100, the client device 110 may be used by a user to change or set properties or settings of the operation of the vaporizer device 105. The client device 110 may include a laptop computer, a desktop computer, a smartphone, and a tablet, among others. The client device 110 may include a processor 175, memory 180, a user interface element 185, and a communication interface 190. The processor 175 may include the functionalities of the main processor 420 or the CPU 421 detailed herein in conjunction with FIGS. 4C and 4D. The memory 180 may include the functionalities of the main memory 428, and cache memory 440 detailed herein in conjunction with FIGS. 4C and 4D, and may include computer-readable instructions (e.g., application 195) to be processed and executed by the processor 175. The communication interface 190 may include the functionalities of the network interface 418 detailed herein in conjunction with FIGS. 4C and 4D. The user interface element 185 may include the functionalities of the I/O control 423, display devices 424*a-n*, keyboard 426, pointing device 427, I/O devices 430*a-n* detailed herein in conjunction with FIGS. 4C and 4D.

The application 195 executed on the client device 110 may be used to set various functionalities of the vaporizer device 105. The functionalities of the vaporization device 105 that may be set by the application 195 may include: the amount of electrical energy and time at which to provide the electrical energy from the power source 140 to the heating element 145; the amount of thermal energy, the temperature, and the time at which to provide the thermal energy from the heating element 145 to the ceramic chamber housing the liquid cartridge 150; and the amount and the rate of the substance in liquid form from the liquid cartridge 150 is to be provided to the ceramic chamber housing heated by the heating element 145. The application 195 may provide a graphical user interface to the user of the client device 110 for setting the various functionalities of the vaporizer device 105. Once set, the client device 110 may transmit the settings via the network 115 to the vaporizer device 105. In response to receipt, the processor 120 of the vaporizer device 105 may save and store the received settings as settings 165.

Figure 2:
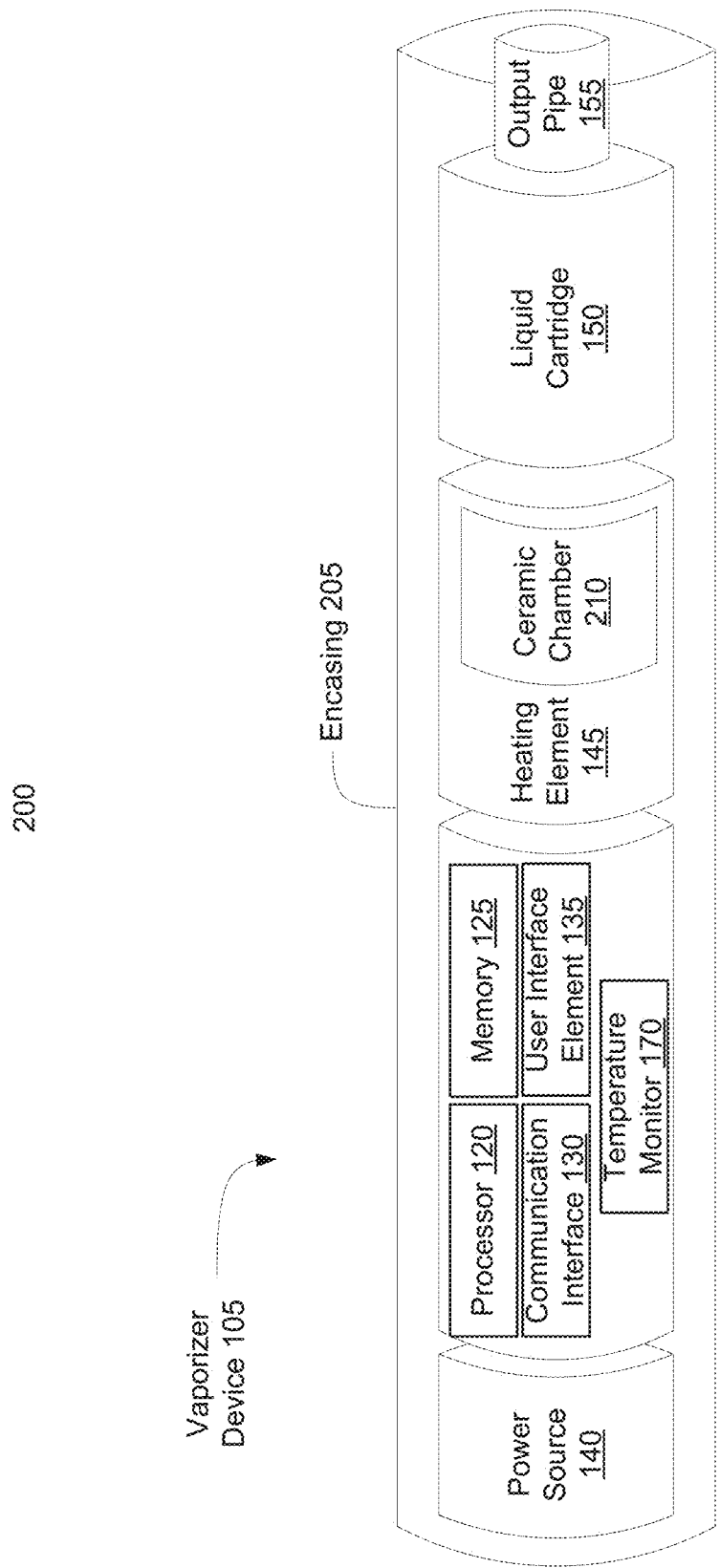
FIG. 2 is a block diagram depicting an apparatus for a vaporization and inhaler apparatus with a heating mechanism, according to an illustrative embodiment.

Referring now to FIG. 2, FIG. 2 depicts an apparatus 200 for a vaporization and inhaler apparatus with a heating mechanism. The apparatus 200 may include an encasing 205. In some implementations, the encasing 205 for the apparatus 200 may be 5 cm to 250 cm in length, 1 cm to 20 cm in width, and 1 cm to 25 cm in height. The encasing 205 may house the vaporizer device 105 and other materials for electrically or thermally sealing the components of the vaporizer device 105 from one another. In the embodiment depicted in FIG. 2, the encasing 205 may include a separate housing for the power source 140, a separate housing for the processor 120, the memory 125, the communication device 130, the user interface element 135, and the temperature monitor 170, a separate housing for the heating element 145 and a ceramic chamber 210, a separate housing for the liquid cartridge 150, and a separate housing for the output pipe 155. In some embodiments, the output pipe 155 may be an opening in the encasing 205 connecting the liquid cartridge 150 to the outside air. In some embodiments, the output pipe 155 may be an opening in the encasing 205 connecting the ceramic chamber 210 to the outside air. In some embodiments, the output pipe 155 may be an opening in the encasing 205 connecting the ceramic chamber 210 and the liquid cartridge 150 to the outside air. In some embodiments, the ceramic chamber 210 may be part of the liquid cartridge 150. In some embodiments, the ceramic chamber 210 may be part of the heating element 145. In some embodiments, the ceramic chamber 210 may be surrounded by or impregnated with glass. The glass may have a higher thermal conductivity than the material in the ceramic chamber, allowing the glass to heat the ceramic chamber 210 at a higher rate. Use of the glass with or in the ceramic chamber 210 may reduce the initialization time to get to the temperature to vaporize the substance in liquid form in the liquid cartridge 150. The encasing 205 may separately house or encase each component in various configurations, besides the one depicted in FIG. 2.

Referring now to FIGS. 3A-3G, depicted are vaporization and inhaler apparatuses 300A-300G each with the heating mechanism 145, the liquid cartridge 150, and the ceramic chamber 210 as detailed herein previously. Beginning with FIG. 3A, apparatus 300A may include the liquid cartridge 150 and the heating element 145. The liquid cartridge 150 may include the substance in liquid form 310A. The liquid cartridge 150 may itself be the ceramic chamber 210. The liquid cartridge 150 may be attached or coupled to the heating element 145 at one end. The heating element 145 may include an electrical connector 312. The electrical connector 312 may be electrically coupled to the power source 140. The heating element 145 may convert electrical energy to thermal energy to apply one end of the liquid cartridge. The liquid cartridge 150 can include an outlet 304 for exiting the substance in gaseous form when the substance in liquid form 310A is heated by the heating element 145. The outlet 304 may be a pipe partially extending longitudinally within the liquid cartridge 150.

Figure 3A:
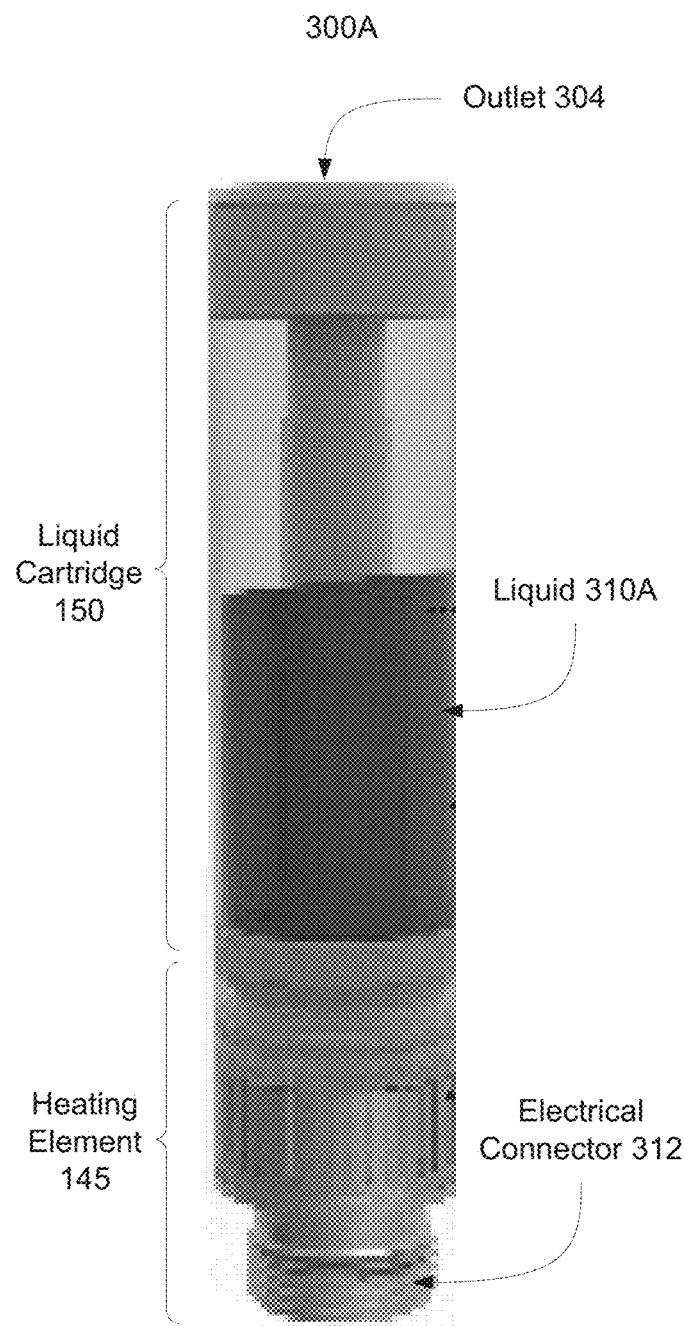
FIG. 3A-3G are block diagrams depicting heating apparatuses with inlets and/or outlets for vaporizing substances in ceramic chambers, according to illustrative embodiments.
Figure 3B:
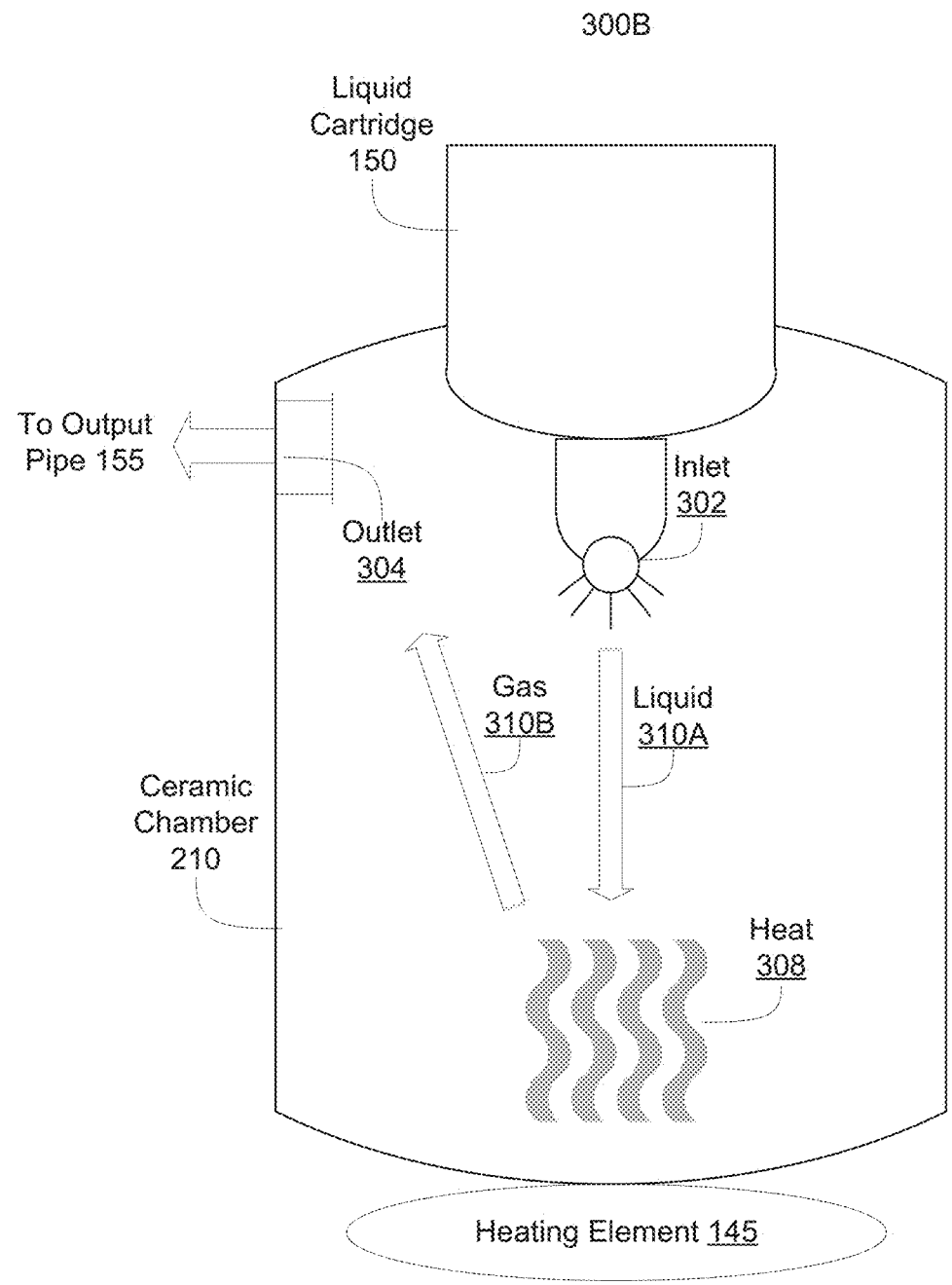

Referring now to FIG. 3B, apparatus 300B may include the ceramic chamber 210 with the outlet 304, the heating element 145, and the liquid cartridge 150 with an inlet 302. The liquid cartridge 150 may be inserted into the ceramic chamber 210. The ceramic chamber 210 may hold one end of the liquid cartridge 150 with the inlet 302. The inlet 302 of the liquid chamber 150 may release the substance in liquid form 310A into the ceramic chamber 210. The release of the substance in liquid form 310A may be automatically controlled by the control module 160 executed on the processor 120. The release of the substance in liquid form 310A may be manually controlled by user interaction with the user interface element 135 (e.g., button press). The heating mechanism 145 may be a heat plate and may be generally along one end of the ceramic chamber 210. The heating mechanism 145 may be electrically coupled to the power source 140. The heating mechanism 145 may convert electrical energy to thermal energy to apply heat 308 to the substance in liquid form 310A through the ceramic chamber 210. Advantageously, with relatively low thermal conductivity, the ceramic chamber 210 may more evenly distribute and slowly apply the thermal energy to the substance in liquid form 310A therein, thereby preventing combustion of the substance. Once heated, the substance in liquid form 310A may undergo partial or flash evaporation to become gaseous form 310B. The outlet 304 of the ceramic chamber 210 may exit the substance in gaseous form 310B to the output pipe 155. In some embodiments, the outlet 304 may include a flap or other obstruction to control the flow of the substance in gaseous form 310B to the output pipe 155. The flap of the outlet 304 may be automatically or manually controlled.

Figure 3C:
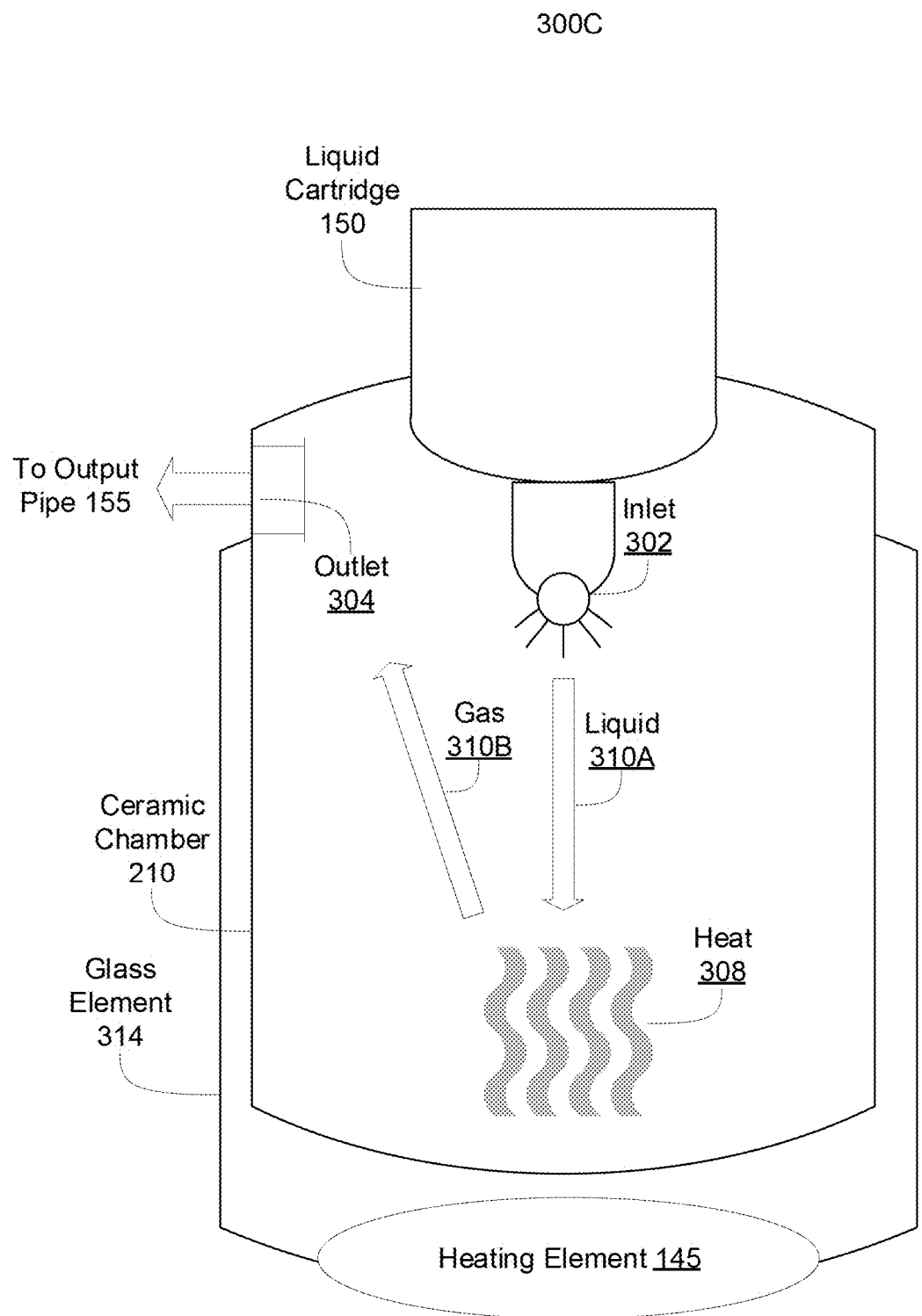

In FIG. 3C, apparatus 300C may be similar to the apparatus 300B with the ceramic chamber 210 with the outlet 304, the heating element 145, and the liquid cartridge 150 with the inlet 302. The apparatus 300C may differ from the apparatus 300B in that the apparatus 300C may include a glass element 314 surrounding the ceramic chamber 210. In some embodiments, the glass element 314 may be impregnated into the ceramic chamber 210. The glass element 314 may be thermally coupled to the heating element 145. The glass element 314 may have a relatively higher thermal conductivity than the ceramic chamber 210. The glass element 314 may be used to initially heat the ceramic chamber 210 at a faster rate. Heating applied to the ceramic chamber 210 by the glass element 314 may yield a shorter initialization time for converting the substance from liquid form 310A to gaseous form 310B. Simultaneously, the ceramic chamber 210 may distribute the thermal energy applied to the substance in liquid form 310A, thereby lowering the likelihood of combustion or burning of the substance.

Figure 3D:
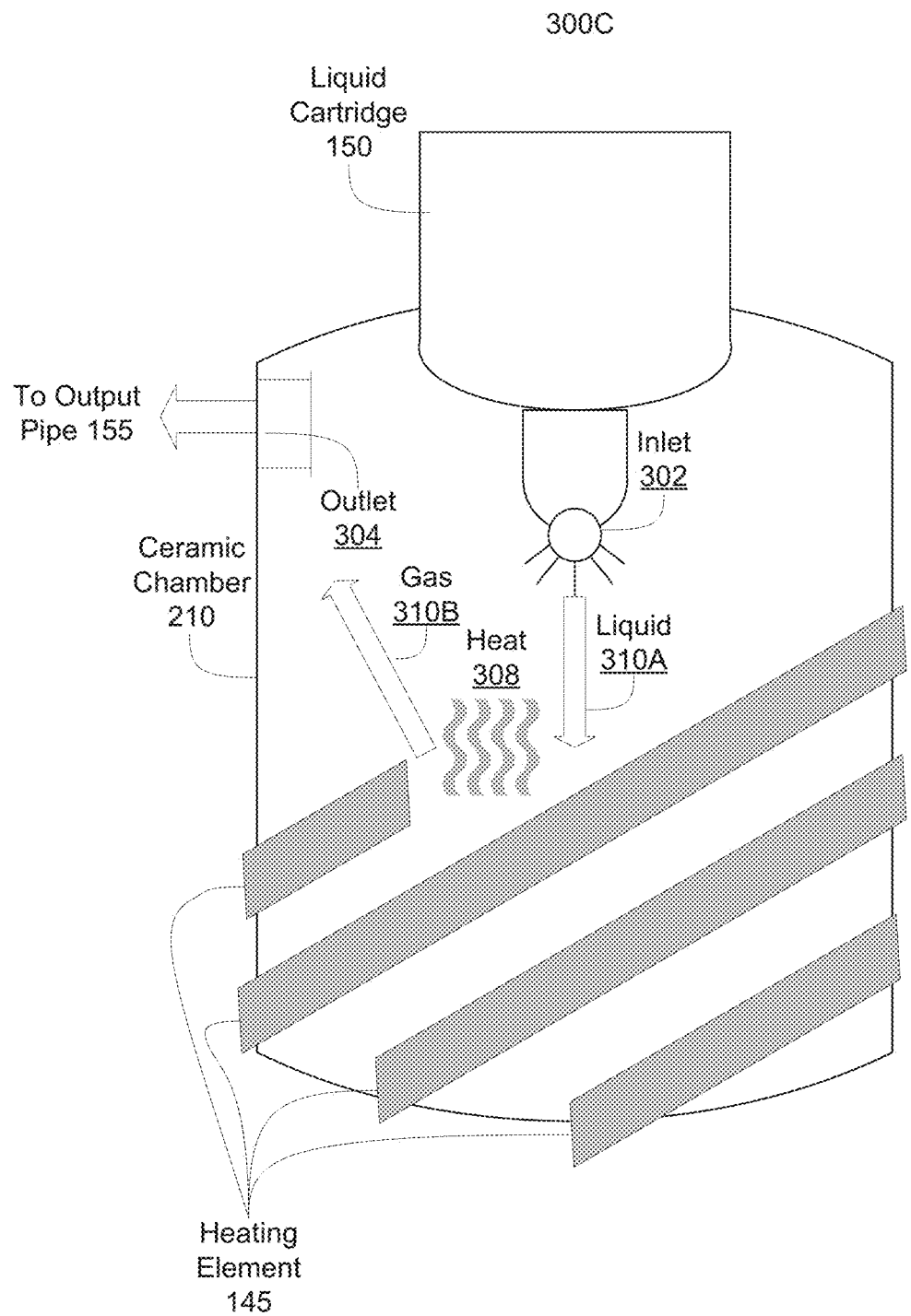

Next to FIG. 3D, apparatus 300D may be similar to the apparatus 300B with the ceramic chamber 210 with the outlet 304, the heating element 145, and the liquid cartridge 150 with the inlet 302. In apparatus 300D, the heating element 315 may be a thermally conductive coil surrounding the ceramic chamber 210, as opposed to being a heat plate. The coil may be electrically coupled to the power source 145 and thermally coupled to the ceramic chamber 210. In some embodiments, the coil may be wrapped around the ceramic chamber 210 longitudinally about the length of the ceramic chamber 210. In some embodiments, the coil may be wrapped around the ceramic chamber 210 laterally about the height or width of the ceramic chamber 210. In some embodiments, the coil may be wrapped around the ceramic chamber 210 at an inclined or declined angle. Having a coil as the heating element 315 in this manner may apply the heat more evenly throughout the ceramic chamber 210, thereby yielding a more controlled evaporation of the substance from liquid form 310A to gaseous form 310B.

Figure 3E:
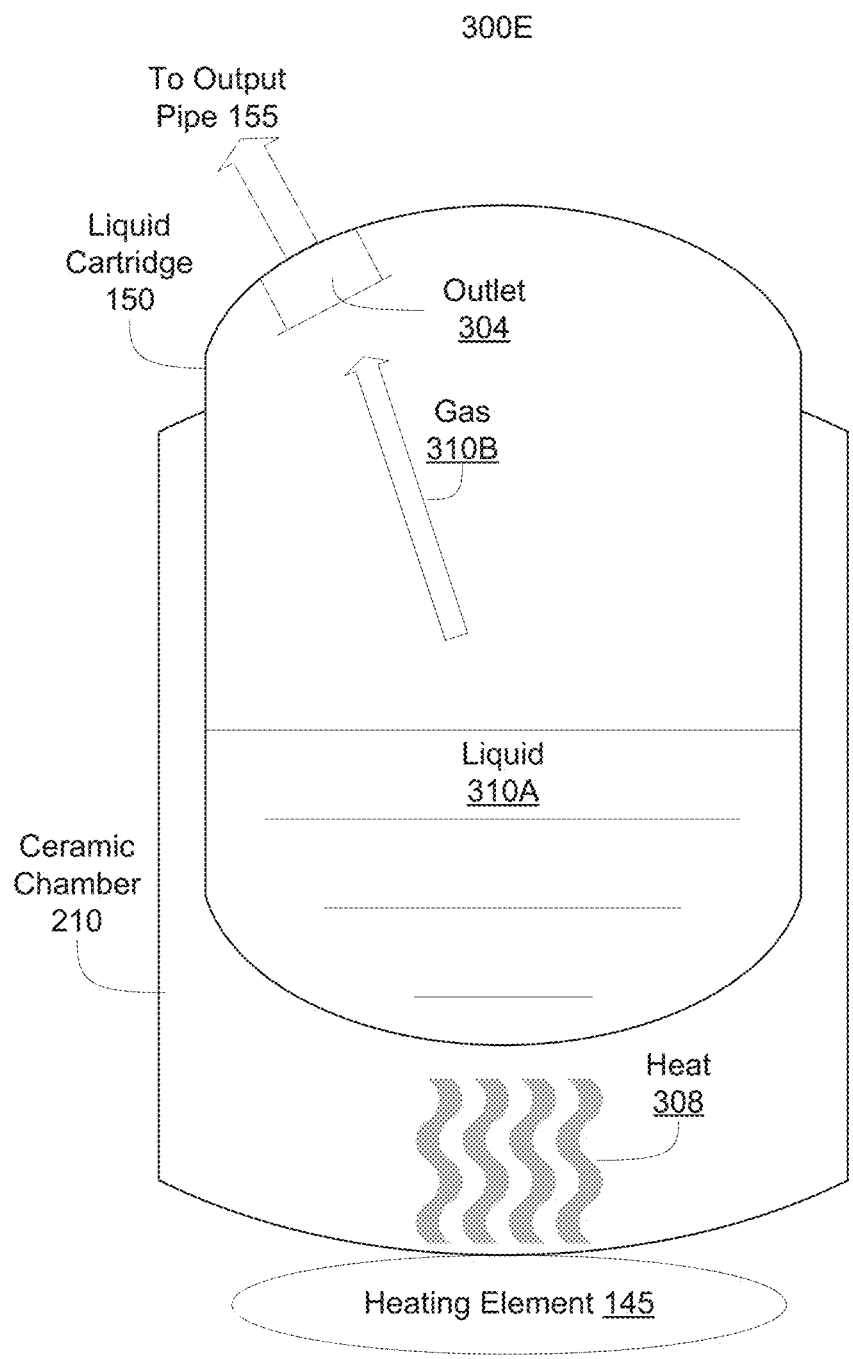

Referring now to FIG. 3E, apparatus 300E may include the ceramic chamber 210, the heating element 145, and the liquid cartridge 150 with the outlet 304. The apparatus 300E may be similar to apparatus 300B. The liquid cartridge 150 may be inserted into the ceramic chamber 210 at one end. In some implementations, the ceramic chamber can include an opening sized to receive the liquid cartridge. In some implementations, the ceramic chamber can include an opening sized to receive the liquid cartridge such that the sidewalls of the liquid cartridge are encompassed by and/or in contact with or close proximity to adjacent walls of the ceramic chamber. The ceramic chamber 210 may hold or accommodate one end of the liquid cartridge 150. In some embodiments, the ceramic chamber 210 may include a physical contact for accommodating the liquid cartridge 150 within. The heating mechanism 145 may be a heat plate and may be generally along one end of the ceramic chamber 210. The heating mechanism 145 may be electrically coupled to the power source 140. The heating mechanism 145 may convert electrical energy to thermal energy to apply heat 308 to the ceramic chamber 210. In contrast with apparatuses 300B, however, the apparatus 300E may lack the inlet 302, may have the outlet 304 at the liquid cartridge 150 as opposed to the ceramic chamber 210, and may have the heating element 145 heat the substance in liquid form 310A without release into the ceramic chamber 210. In some embodiments, the ceramic chamber 210 may in turn be physically coupled to the liquid cartridge 150. The heating element 145 may apply heat 308 to the substance in liquid form 310A through the ceramic chamber 210 to the liquid cartridge 150f from one end of the liquid cartridge 150. Once heated, the substance in liquid form 310A in the liquid cartridge 150 may be converted to gaseous form 310B. The substance in gaseous form 310B may exit the liquid cartridge 150 via the outlet 304 located at the liquid cartridge 150 to the output pipe 155 for inhaled consumption by the user of the vaporizer device 105.

Figure 3F:
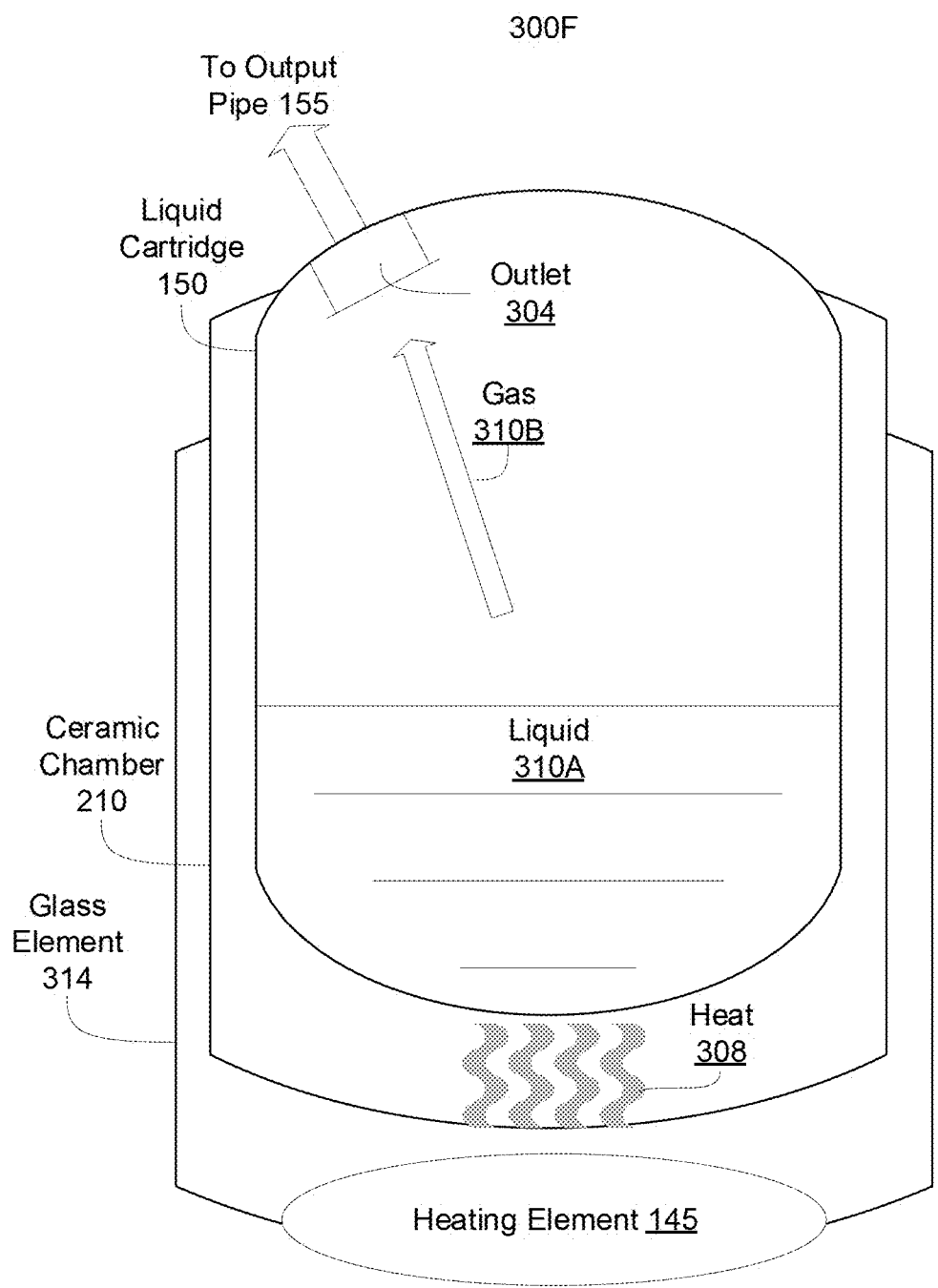

Referring now to FIG. 3F, apparatus 300F may be similar to the apparatus 300E with the ceramic chamber 210, the heating element 145, and the liquid cartridge 150 with the outlet 304. Apparatus 300F may differ from the apparatus 300E in that the apparatus 300F may include a glass element 314 surrounding the ceramic chamber 210. In some embodiments, the glass element 314 may be impregnated into the ceramic chamber 210. The glass element 314 may be thermally coupled to the heating element 145. In some embodiments, the ceramic chamber 210 may in turn be physically coupled to the liquid cartridge 150. The glass element 314 may have a relatively higher thermal conductivity than the ceramic chamber 210. The glass element 314 may be used to initially heat the ceramic chamber 210 and the liquid cartridge 150 at a faster rate. Heating applied to the ceramic chamber 210 and the liquid cartridge 150 by the glass element 314 may yield a shorter initialization time for starting the consumption of the substance in gaseous form 310B. Simultaneously, the ceramic chamber 210 may evenly distribute the thermal energy applied to the liquid cartridge 150 and the substance in liquid form 310A therein, thereby lowering the likelihood of combustion of the substance.

Figure 3G:
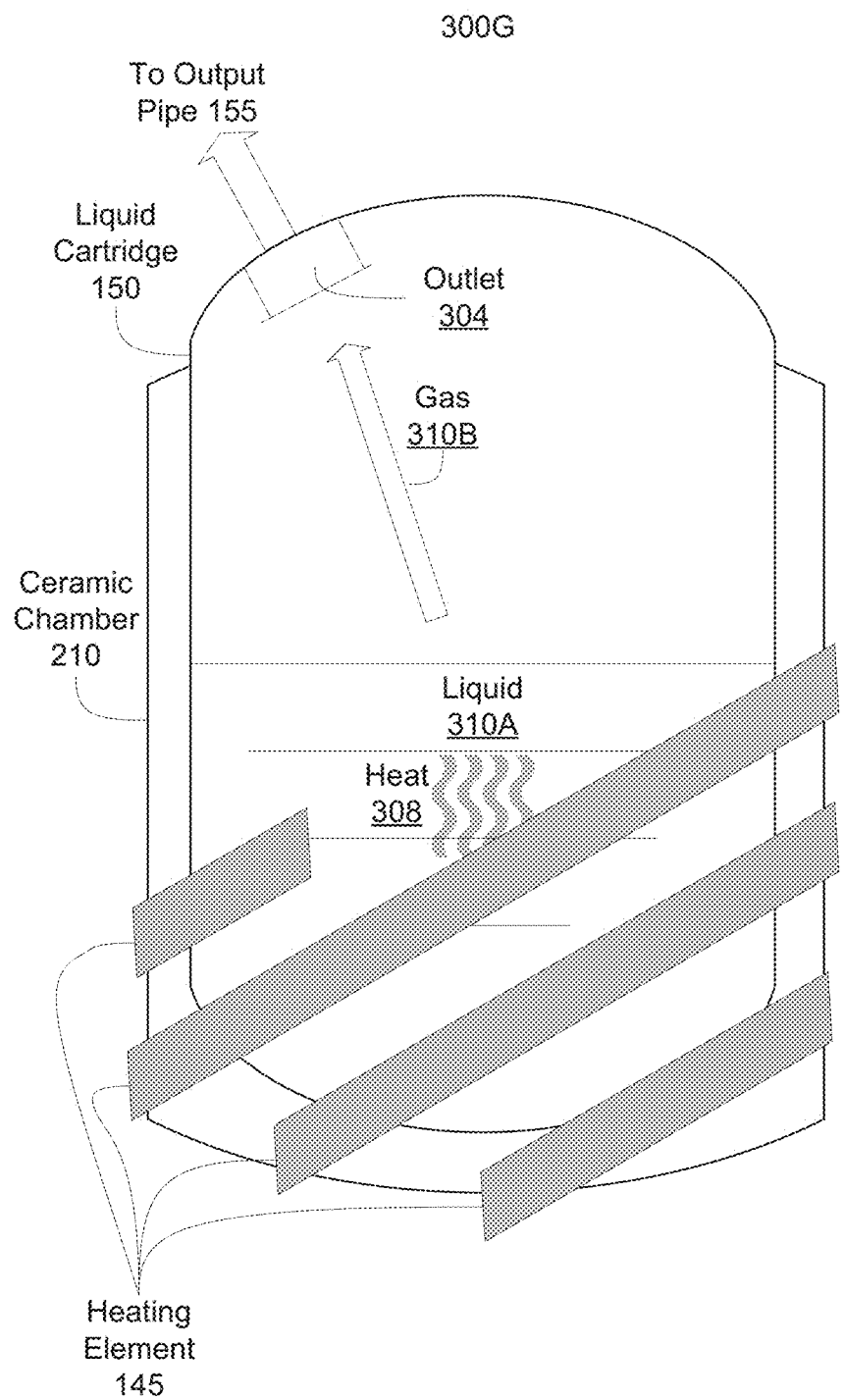

Referring now to FIG. 3G, apparatus 300G may be similar to the apparatus 300E with the ceramic chamber 210, the heating element 145, and the liquid cartridge 150 with the outlet 304. In apparatus 300G, the heating element 315 may be a thermally conductive coil surrounding the ceramic chamber 210, as opposed to being a heat plate. The coil may be electrically coupled to the power source 145 and thermally coupled to the ceramic chamber 210. In some embodiments, the coil may be physically wrapped around the ceramic chamber 210 longitudinally about the length of the ceramic chamber 210. In some embodiments, the coil may be physically wrapped around the ceramic chamber 210 laterally about the height or width of the ceramic chamber 210. In some embodiments, the coil may be physically wrapped around the ceramic chamber 210 at an inclined or declined angle. In some embodiments, the ceramic chamber 210 may in turn be physically or thermally coupled to the liquid cartridge 150. Having a coil as the heating element 315 in this manner may apply the heat more evenly throughout the ceramic chamber 210, thereby yielding a more controlled evaporation of the substance from liquid form 310A to gaseous form 310B.

B. Computing and Network Environment

Figure 4A:
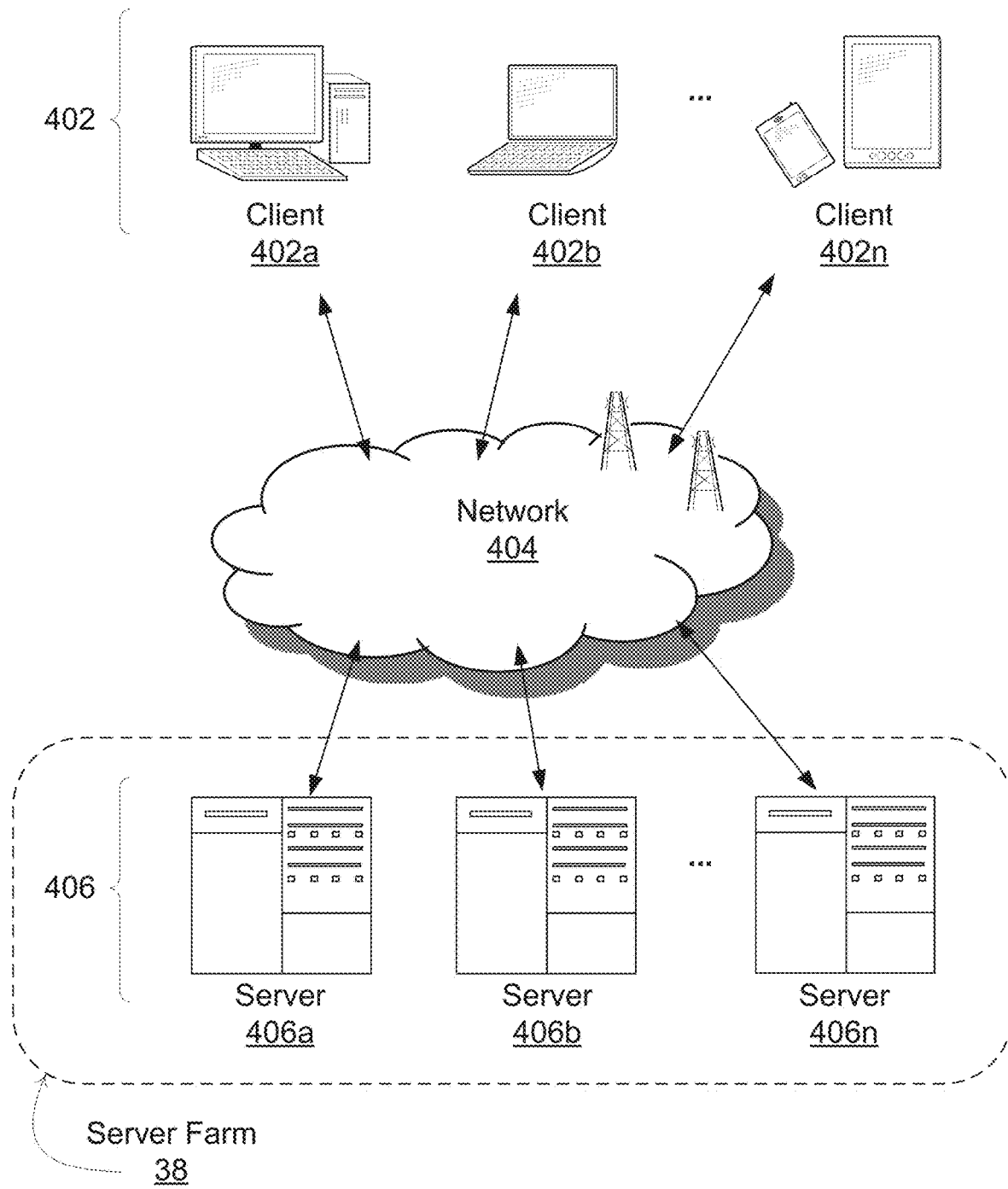
FIG. 4A is a block diagram depicting an embodiment of a network environment comprising client devices in communication with server devices.

It may be helpful to describe aspects of the operating environment as well as associated system components (e.g., hardware elements) in connection with the methods and systems described herein. Referring to FIG. 4A, an embodiment of a network environment is depicted. In brief overview, the illustrated exploring network environment includes one or more clients 402a-402n (also generally referred to as local machine(s) 402, client(s) 402, client node(s) 402, client machine(s) 402, client computer(s) 402, client device(s) 402, endpoint(s) 402, or endpoint node(s) 402) in communication with one or more servers 406a-406n (also generally referred to as server(s) 406, node 406, or remote machine(s) 406) via one or more networks 404. In some embodiments, a client 402 has the capacity to function as both a client node seeking access to resources provided by a server and as a server providing access to hosted resources for other clients 402a-402n.

Although FIG. 4A shows a network 404 between the clients 402 and the servers 406, the clients 402 and the servers 406 may be on the same network 404. In some embodiments, there are multiple networks 404 between the clients 402 and the servers 406. In one of these embodiments, a network 404' (not shown) may be a private network and a network 404 may be a public network. In another of these embodiments, a network 404 may be a private network and a network 404' a public network. In still another of these embodiments, networks 404 and 404' may both be private networks.

The network 404 may be connected via wired or wireless links. Wired links may include Digital Subscriber Line (DSL), coaxial cable lines, or optical fiber lines. The wireless links may include BLUETOOTH, Wi-Fi, NFC, RFID Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 404 may be any type and/or form of network. The geographical scope of the network 404 may vary widely and the network 404 can be a body area network (BAN), a personal area network (PAN), a local-area network (LAN), e.g. Intranet, a metropolitan area network (MAN), a wide area network (WAN), or the Internet. The topology of the network 404 may be of any form and may include, e.g., any of the following: point-to-point, bus, star, ring, mesh, or tree. The network 404 may be an overlay network, which is virtual and sits on top of one or more layers of other networks 404'. The network 404 may be of any such network topology as known to those ordinarily skilled in the art capable of supporting the operations described herein. The network 404 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 404 may be a type of a broadcast network, a telecommunications network, a data communication network, or a computer network.

In some embodiments, the system may include multiple, logically-grouped servers 406. In one of these embodiments, the logical group of servers may be referred to as a server farm 38 or a machine farm 38. In another of these embodiments, the servers 406 may be geographically dispersed. In other embodiments, a machine farm 38 may be administered as a single entity. In still other embodiments, the machine farm 38 includes a plurality of machine farms 38. The servers 406 within each machine farm 38 can be heterogeneous—one or more of the servers 406 or machines 406 can operate according to one type of operating system platform (e.g., WINDOWS NT, manufactured by Microsoft Corp. of Redmond, Wash.), while one or more of the other servers 406 can operate on according to another type of operating system platform (e.g., Unix, Linux, or Mac OS X).

In one embodiment, servers 406 in the machine farm 38 may be stored in high-density rack systems, along with associated storage systems, and located in an enterprise data center. In this embodiment, consolidating the servers 406 in this way may improve system manageability, data security, the physical security of the system, and system performance by locating servers 406 and high performance storage systems on localized high performance networks. Centralizing the servers 406 and storage systems and coupling them with advanced system management tools allows more efficient use of server resources.

The servers 406 of each machine farm 38 do not need to be physically proximate to another server 406 in the same machine farm 38. Thus, the group of servers 406 logically grouped as a machine farm 38 may be interconnected using a wide-area network (WAN) connection or a metropolitan-area network (MAN) connection. For example, a machine farm 38 may include servers 406 physically located in different continents or different regions of a continent, country, state, city, campus, or room. Data transmission speeds between servers 406 in the machine farm 38 can be increased if the servers 406 are connected using a local-area network (LAN) connection or some form of direct connection. Additionally, a heterogeneous machine farm 38 may include one or more servers 406 operating according to a type of operating system, while one or more other servers 406 execute one or more types of hypervisors rather than operating systems. In these embodiments, hypervisors may be used to emulate virtual hardware, partition physical hardware, virtualized physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 406 may comprise components, subsystems and modules to support one or more management services for the machine farm 38. In one of these embodiments, one or more servers 406 provide functionality for management of dynamic data, including techniques for handling failover, data replication, and increasing the robustness of the machine farm 38. Each server 406 may communicate with a persistent store and, in some embodiments, with a dynamic store.

Server 406 may be a file server, application server, web server, proxy server, appliance, network appliance, gateway, gateway server, virtualization server, deployment server, SSL VPN server, or firewall. In one embodiment, the server 406 may be referred to as a remote machine or a node. In another embodiment, a plurality of nodes 290 may be in the path between any two communicating servers.

Figure 4B:
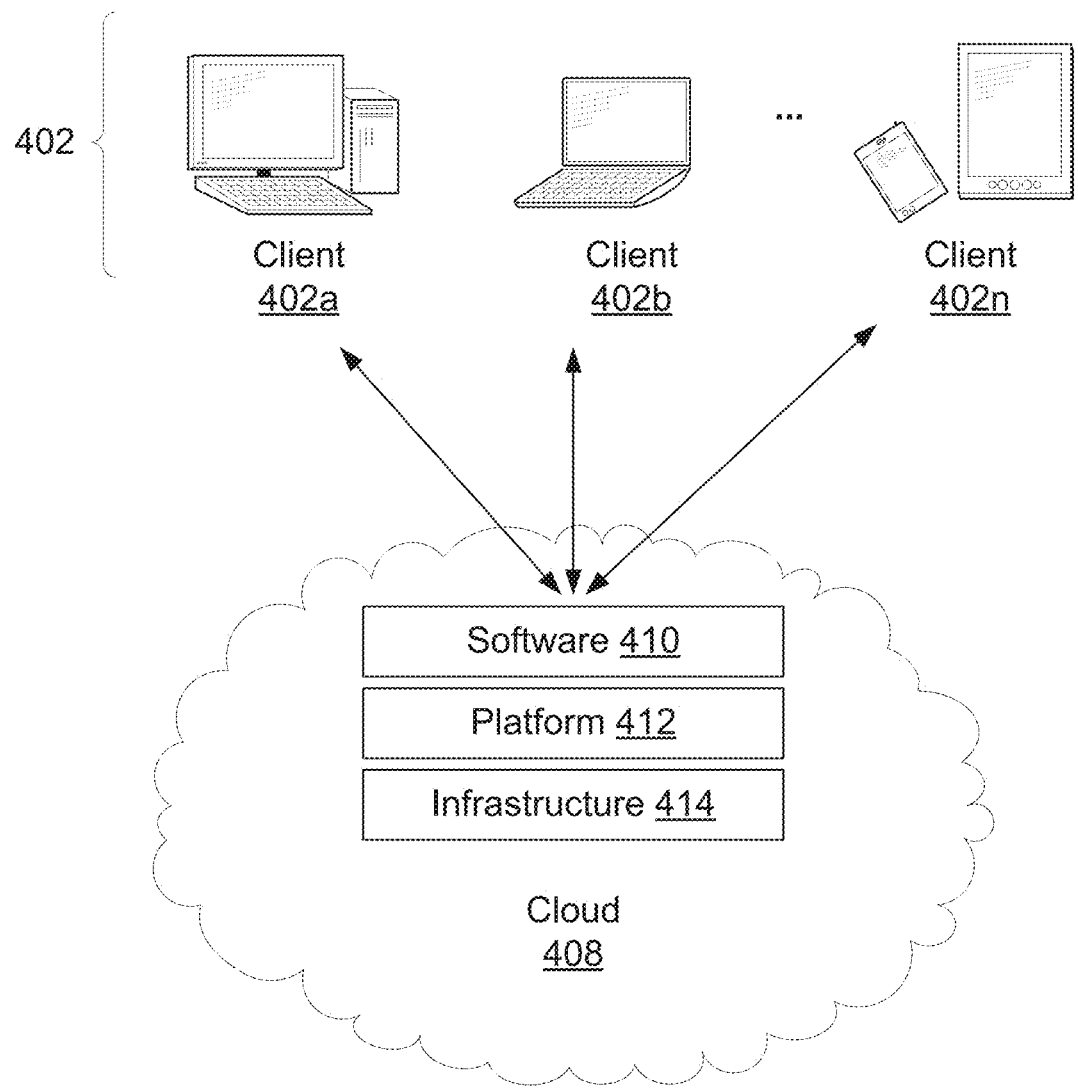
FIG. 4B is a block diagram depicting a cloud computing environment comprising client devices in communication with a cloud service provider.

Referring to FIG. 4B, a cloud computing environment is depicted. A cloud computing environment may provide client 402 with one or more resources provided by a network environment. The cloud computing environment may include one or more clients 402a-402n, in communication with the cloud 408 over one or more networks 404. Clients 402 may include, e.g., thick clients, thin clients, and zero clients. A thick client may provide at least some functionality even when disconnected from the cloud 408 or servers 406. A thin client or a zero client may depend on the connection to the cloud 408 or server 406 to provide functionality. A zero client may depend on the cloud 408 or other networks 404 or servers 406 to retrieve operating system data for the client device. The cloud 408 may include back end platforms, e.g., servers 406, storage, server farms or data centers.

The cloud 408 may be public, private, or hybrid. Public clouds may include public servers 406 that are maintained by third parties to the clients 402 or the owners of the clients. The servers 406 may be located off-site in remote geographical locations as disclosed above or otherwise. Public clouds may be connected to the servers 406 over a public network. Private clouds may include private servers 406 that are physically maintained by clients 402 or owners of clients. Private clouds may be connected to the servers 406 over a private network 404. Hybrid clouds 408 may include both the private and public networks 404 and servers 406.

The cloud 408 may also include a cloud based delivery, e.g. Software as a Service (SaaS) 410, Platform as a Service (PaaS) 412, and Infrastructure as a Service (IaaS) 414. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS may also include data storage providers, e.g. DROPBOX provided by Dropbox, Inc. of San Francisco, Calif., Microsoft SKYDRIVE provided by Microsoft Corporation, Google Drive provided by Google Inc., or Apple ICLOUD provided by Apple Inc. of Cupertino, Calif.

Clients 402 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 402 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 402 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 402 may also access SaaS resources through smartphone or tablet applications, including, e.g., Salesforce Sales Cloud, or Google Drive app. Clients 402 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 4C:
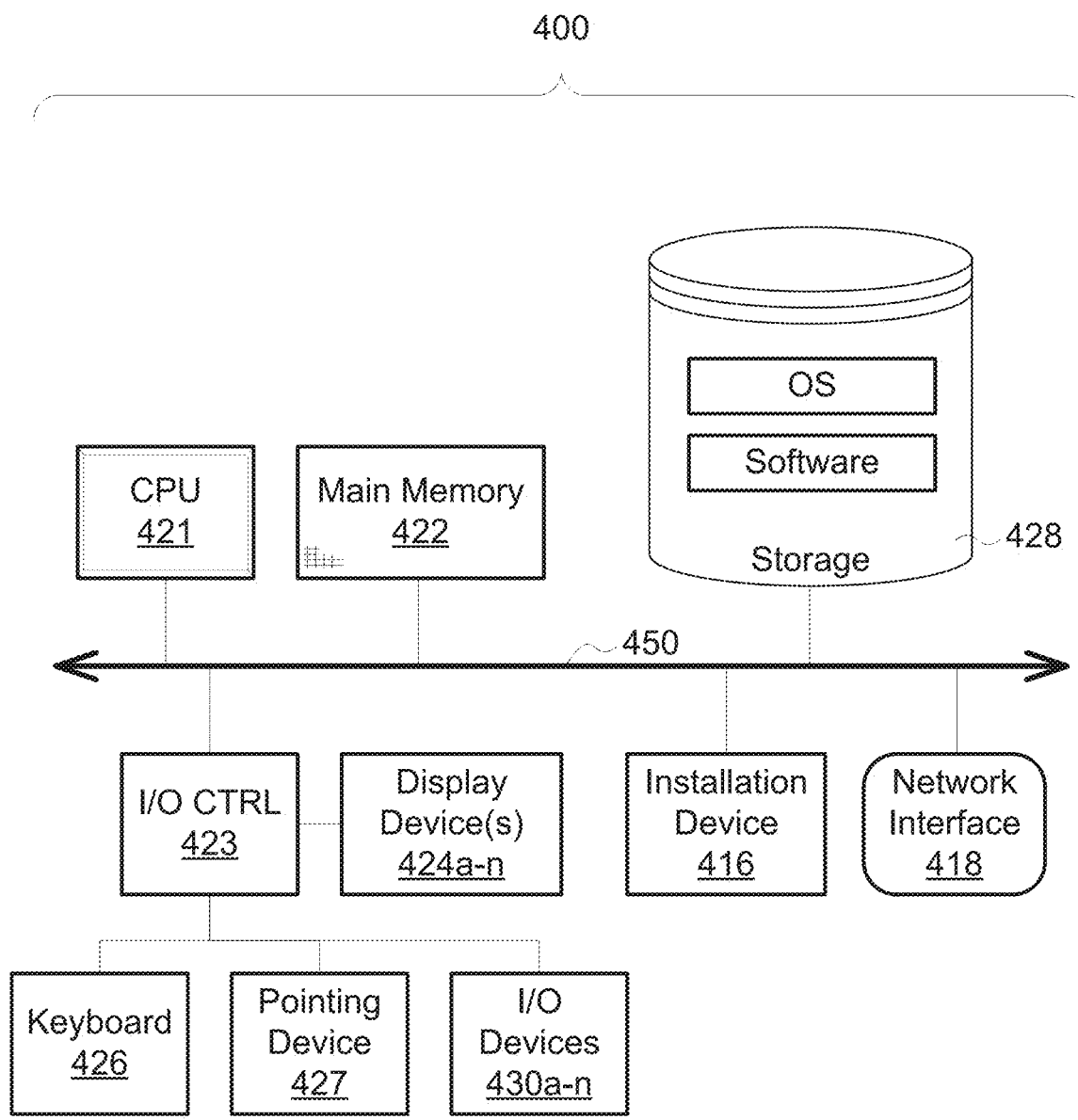
FIGS. 4C and 4D are block diagrams depicting embodiments of computing devices useful in connection with the methods and systems described herein.
Figure 4D:
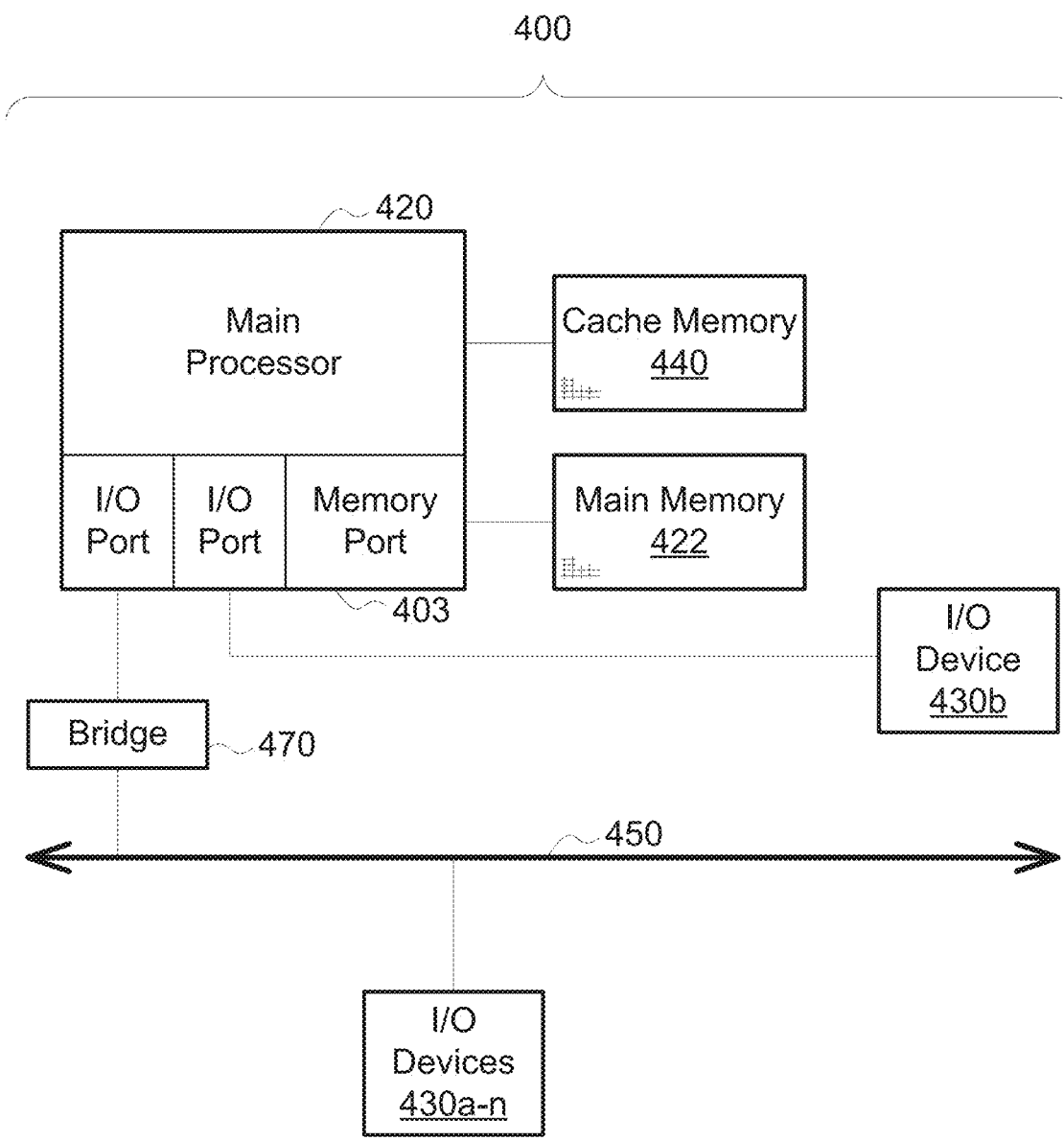

The client 402 and server 406 may be deployed as and/or executed on any type and form of computing device, e.g. a computer, network device or appliance capable of communicating on any type and form of network and performing the operations described herein. FIGS. 1C and 1D depict block diagrams of a computing device 400 useful for practicing an embodiment of the client 402 or a server 406. As shown in FIGS. 1C and 1D, each computing device 400 includes a central processing unit 421, and a main memory unit 422. As shown in FIG. 4C, a computing device 400 may include a storage device 428, an installation device 416, a network interface 418, an I/O controller 423, display devices 424a-424n, a keyboard 426 and a pointing device 427, e.g. a mouse. The storage device 428 may include, without limitation, an operating system, and/or software of a vaporization system 420. As shown in FIG. 4D, each computing device 400 may also include additional optional elements, e.g. a memory port 403, a bridge 470, one or more input/output devices 430a-430n (generally referred to using reference numeral 430), and a cache memory 440 in communication with the central processing unit 421.

The central processing unit 421 is any logic circuitry that responds to and processes instructions fetched from the main memory unit 422. In many embodiments, the central processing unit 421 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 400 may be based on any of these processors, or any other processor capable of operating as described herein. The central processing unit 421 may utilize instruction level parallelism, thread level parallelism, different levels of cache, and multi-core processors. A multi-core processor may include two or more processing units on a single computing component. Examples of multi-core processors include the AMD PHENOM IIX2, INTEL CORE i5 and INTEL CORE i7.

Main memory unit 422 may include one or more memory chips capable of storing data and allowing any storage location to be directly accessed by the microprocessor 421. Main memory unit 422 may be volatile and faster than storage 428 memory. Main memory units 422 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 422 or the storage 428 may be non-volatile; e.g., non-volatile read access memory (NVRAM), flash memory non-volatile static RAM (nvSRAM), Ferro-electric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 422 may be based on any of the above described memory chips, or any other available memory chips capable of operating as described herein. In the embodiment shown in FIG. 4C, the processor 421 communicates with main memory 422 via a system bus 450 (described in more detail below). FIG. 4D depicts an embodiment of a computing device 400 in which the processor communicates directly with main memory 422 via a memory port 403. For example, in FIG. 4D the main memory 422 may be DRDRAM.

FIG. 4D depicts an embodiment in which the main processor 421 communicates directly with cache memory 440 via a secondary bus, sometimes referred to as a backside bus. In other embodiments, the main processor 421 communicates with cache memory 440 using the system bus 450. Cache memory 440 typically has a faster response time than main memory 422 and is typically provided by SRAM, BSRAM, or EDRAM. In the embodiment shown in FIG. 4D, the processor 421 communicates with various I/O devices 430 via a local system bus 450. Various buses may be used to connect the central processing unit 421 to any of the I/O devices 430, including a PCI bus, a PCI-X bus, or a PCI-Express bus, or a NuBus. For embodiments in which the I/O device is a video display 424, the processor 421 may use an Advanced Graphics Port (AGP) to communicate with the display 424 or the I/O controller 423 for the display 424. FIG. 4D depicts an embodiment of a computer 400 in which the main processor 421 communicates directly with I/O device 430b or other processors 421' via HYPERTRANSPORT, RAPIDIO, or INFINIBAND communications technology. FIG. 4D also depicts an embodiment in which local busses and direct communication are mixed: the processor 421 communicates with I/O device 430a using a local interconnect bus while communicating with I/O device 430b directly.

A wide variety of I/O devices 430a-430n may be present in the computing device 400. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 430a-430n may include a combination of multiple input or output devices, including, e.g., Microsoft KINECT, Nintendo Wiimote for the WII, Nintendo WII U GAMEPAD, or Apple IPHONE. Some devices 430a-430n allow gesture recognition inputs through combining some of the inputs and outputs. Some devices 430a-430n provides for facial recognition which may be utilized as an input for different purposes including authentication and other commands. Some devices 430a-430n provides for voice recognition and inputs, including, e.g., Microsoft KINECT, SIRI for IPHONE by Apple, Google Now or Google Voice Search.

Additional devices 430a-430n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 430a-430n, display devices 424a-424n or group of devices may be augment reality devices. The I/O devices may be controlled by an I/O controller 423 as shown in FIG. 4C. The I/O controller may control one or more I/O devices, such as, e.g., a keyboard 426 and a pointing device 427, e.g., a mouse or optical pen. Furthermore, an I/O device may also provide storage and/or an installation medium 416 for the computing device 400. In still other embodiments, the computing device 400 may provide USB connections (not shown) to receive handheld USB storage devices. In further embodiments, an I/O device 430 may be a bridge between the system bus 450 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 424a-424n may be connected to I/O controller 423. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 424a-424n may also be a head-mounted display (HMD). In some embodiments, display devices 424a-424n or the corresponding I/O controllers 423 may be controlled through or have hardware support for OPENGL or DIRECTX API or other graphics libraries.

In some embodiments, the computing device 400 may include or connect to multiple display devices 424a-424n, which each may be of the same or different type and/or form. As such, any of the I/O devices 430a-430n and/or the I/O controller 423 may include any type and/or form of suitable hardware, software, or combination of hardware and software to support, enable or provide for the connection and use of multiple display devices 424a-424n by the computing device 400. For example, the computing device 400 may include any type and/or form of video adapter, video card, driver, and/or library to interface, communicate, connect or otherwise use the display devices 424a-424n. In one embodiment, a video adapter may include multiple connectors to interface to multiple display devices 424a-424n. In other embodiments, the computing device 400 may include multiple video adapters, with each video adapter connected to one or more of the display devices 424a-424n. In some embodiments, any portion of the operating system of the computing device 400 may be configured for using multiple displays 424a-424n. In other embodiments, one or more of the display devices 424a-424n may be provided by one or more other computing devices 400a or 400b connected to the computing device 400, via the network 404. In some embodiments software may be designed and constructed to use another computer's display device as a second display device 424a for the computing device 400. For example, in one embodiment, an Apple iPad may connect to a computing device 400 and use the display of the device 400 as an additional display screen that may be used as an extended desktop. One ordinarily skilled in the art will recognize and appreciate the various ways and embodiments that a computing device 400 may be configured to have multiple display devices 424a-424n.

Referring again to FIG. 4C, the computing device 400 may comprise a storage device 428 (e.g. one or more hard disk drives or redundant arrays of independent disks) for storing an operating system or other related software, and for storing application software programs such as any program related to the software 420 for the vaporization system. Examples of storage device 428 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 428 may be non-volatile, mutable, or read-only. Some storage device 428 may be internal and connect to the computing device 400 via a bus 450. Some storage device 428 may be external and connect to the computing device 400 via an I/O device 430 that provides an external bus. Some storage device 428 may connect to the computing device 400 via the network interface 418 over a network 404, including, e.g., the Remote Disk for MACBOOK AIR by Apple. Some client devices 400 may not require a non-volatile storage device 428 and may be thin clients or zero clients 402. Some storage device 428 may also be used as an installation device 416, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 400 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 402. An application distribution platform may include a repository of applications on a server 406 or a cloud 408, which the clients 402a-402n may access over a network 404. An application distribution platform may include application developed and provided by various developers. A user of a client device 402 may select, purchase and/or download an application via the application distribution platform.

Furthermore, the computing device 400 may include a network interface 418 to interface to the network 404 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 400 communicates with other computing devices 400' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 418 may comprise a built-in network adapter, network interface card, PCMCIA network card, EXPRESSCARD network card, card bus network adapter, wireless network adapter, USB network adapter, modem or any other device suitable for interfacing the computing device 400 to any type of network capable of communication and performing the operations described herein.

A computing device 400 of the sort depicted in FIGS. 1B and 1C may operate under the control of an operating system, which controls scheduling of tasks and access to system resources. The computing device 400 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computer system 400 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 400 has sufficient processor power and memory capacity to perform the operations described herein. In some embodiments, the computing device 400 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 400 is a gaming system. For example, the computer system 400 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Wash.

In some embodiments, the computing device 400 is a digital audio player such as the Apple IPOD, IPOD Touch, and IPOD NANO lines of devices, manufactured by Apple Computer of Cupertino, Calif. Some digital audio players may have other functionality, including, e.g., a gaming system or any functionality made available by an application from a digital application distribution platform. For example, the IPOD Touch may access the Apple App Store. In some embodiments, the computing device 400 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 400 is a tablet e.g. the IPAD line of devices by Apple; GALAXY TAB family of devices by Samsung; or KINDLE FIRE, by Amazon.com, Inc. of Seattle, Wash. In other embodiments, the computing device 400 is an eBook reader, e.g. the KINDLE family of devices by Amazon.com, or NOOK family of devices by Barnes & Noble, Inc. of New York City, N.Y.

In some embodiments, the communications device 402 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc; or a Motorola DROID family of smartphones. In yet another embodiment, the communications device 402 is a laptop or desktop computer equipped with a web browser and a microphone and speaker system, e.g. a telephony headset. In these embodiments, the communications devices 402 are web-enabled and can receive and initiate phone calls. In some embodiments, a laptop or desktop computer is also equipped with a webcam or other video capture device that enables video chat and video call. In some embodiments, the communication device 402 is a wearable mobile computing device including but not limited to Google Glass and Samsung Gear.

In some embodiments, the status of one or more machines 402, 406 in the network 404 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the vaporization apparatus and related systems and methods disclosed herein.

In certain embodiments, the controller includes one or more modules structured to functionally execute the operations of the controller. In certain embodiments, the controller includes sensor modules configured to measure time lapse, energy consumption, product consumption, rotation position, a change in rotation, linear position, a change in a linear position, product location, product ingredients, or other vaporization system operating parameters or conditions impacting the use, dispensing, or operation of the vaporization system.

The description herein including modules emphasizes the structural independence of the aspects of the controller, and illustrates one grouping of operations and responsibilities of the controller. Other groupings that execute similar overall operations are understood within the scope of the present application. Modules may be implemented in hardware and/or as computer instructions on a non-transient computer readable storage medium, and modules may be distributed across various hardware or computer based components.

Example and non-limiting module implementation elements include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

Non-limiting examples of various embodiments are disclosed herein. Features from one embodiments disclosed herein may be combined with features of another embodiment disclosed herein as someone of ordinary skill in the art would understand.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A system for modifying operational settings of vaporizer devices, comprising:
 a vaporizer device comprising:
  a liquid cartridge configured to hold a liquid form of a substance;
  a ceramic chamber defining an opening to receive the liquid form of the liquid cartridge;
  a heating element comprising a heat plate to provide thermal energy, the heating element disposed along a first end of the ceramic chamber to apply the thermal energy through the ceramic chamber, the first end opposite of a second end of the ceramic chamber along which the liquid cartridge is disposed;
  a glass element at least partially surrounding an exterior of the ceramic chamber, the glass element thermally coupled with the heating element, the glass element to distribute the thermal energy through the ceramic chamber to convert the liquid form to a gaseous form, the ceramic chamber having an outlet to exhaust the gaseous form of the substance from the opening;
  an encasing housing the heating element, the ceramic chamber, and the liquid cartridge; and
  a processor coupled with memory, configured to:
   receive, from a remote device one or more instructions entered via a graphical user interface displayed on the remote device, to modify one or more of the operational settings of the vaporizer device, the operational settings including: (i) an amount of electrical energy provided by a power source to the heating element of the vaporizer device, (ii) a duration of time of the electrical energy provided by the power source to the heating element, (iii) an amount of thermal energy applied on substances of the liquid cartridge by the heating element, (iv) a duration of time of the thermal energy applied on the substances of the liquid cartridge by the heating element, (v) an amount of liquid to release from the liquid cartridge for heating by the heating element, or (vi) a rate of liquid to release from the liquid cartridge for heating by the heating element; and
   modify, responsive to receiving the one or more instructions to modify from the remote device, the one or more operational settings of the vaporizer device based at least on the one or more instructions.

2. The system of claim 1, wherein the vaporizer device further comprises a glass element having a thermal conductivity greater than the thermal conductivity of the ceramic chamber, to transfer the thermal heat to the ceramic chamber.

3. The system of claim 1, wherein the liquid cartridge further comprises an inlet to release the liquid substance into the opening defined by the ceramic chamber, the liquid substance to undergo partial or flash evaporation via the thermal heat within the opening.

4. The system of claim 1, wherein the vaporizer device further comprises an output pipe fluidly coupled with the outlet of the ceramic chamber to pass the gaseous form of the substance converted from the liquid form.

5. The system of claim 1, wherein the vaporizer device further comprises a sensor configured to acquire sensory data from at least one of the heating element or the liquid cartridge; and
 wherein the processor is further configured to change the thermal energy outputted by the heating element based at least on the sensory data.

6. An apparatus for heating liquid substances for inhaled consumption, comprising:
 a liquid cartridge configured to hold a liquid form of substance;
 a ceramic chamber defining an opening for the liquid cartridge;
 a heating element comprising a heat plate to provide thermal energy, the heating element disposed along a first end of the ceramic chamber to apply the thermal energy through the ceramic chamber, the first end opposite of a second end of the ceramic chamber along which the liquid cartridge is disposed;
 a glass element at least partially surrounding an exterior of the ceramic chamber, the glass element thermally coupled with the heating element to distribute the thermal energy through the ceramic chamber to convert to the liquid form to a gaseous form;
 an outlet defined through the liquid cartridge to exhaust the gaseous form of the substance from the liquid cartridge;
 an encasing housing the heating element, the ceramic chamber, and the liquid cartridge; and
 a processor coupled with memory, configured to control operational settings of at least one of the heating element or the liquid cartridge.

7. The apparatus of claim 6, further comprising a glass element having a thermal conductivity greater than a thermal conductivity of the ceramic chamber, the glass element at least partially surrounding an exterior of the ceramic chamber, the glass element thermally coupled with the heating element to transfer the thermal heat to the ceramic chamber.

8. The apparatus of claim 6, wherein at least a portion of an exterior of the liquid cartridge is encompassed by at least a portion of an interior of the opening defined by the ceramic chamber.

9. The apparatus of claim 6, wherein the processor is further configured to control operational settings of at least one of the heating element or the liquid cartridge based at least on one or more instructions received from a remote device.

10. The apparatus of claim 6, further comprising a sensor configured to acquire sensory data from at least one of the heating element or the liquid cartridge; and
 wherein the processor is further configured to change the thermal energy outputted by the heating element based at least on the sensory data.

11. An apparatus for heating liquid substances for inhaled consumption, comprising:
 a liquid cartridge configured to release a liquid form of substance via an inlet;
 a ceramic chamber having:
  a first end fluidly coupled with the liquid cartridge via the inlet;
  a second end opposite of the first end;
  an opening defined between the first end and the second end, the opening to receive the liquid form of the substance and to convert the liquid form of the substance to a gaseous form; and
  an outlet defined on a sidewall between the first end and second end, the outlet to exhaust the gaseous form of the substance from the opening;
 a heating element comprising a heat plate to provide thermal energy, the heating element disposed along the second end of the ceramic chamber to apply the thermal energy through the ceramic chamber, the second end opposite of the first end of the ceramic chamber along which the liquid cartridge is disposed;

a glass element at least partially surrounding an exterior of the ceramic chamber, the glass element thermally coupled with the heating element, the glass element to thermally coupled with the heating element to distribute the thermal energy through the ceramic chamber to convert the liquid form to the gaseous form; and a processor coupled with memory, configured to control operational settings of at least one of the heating element or the liquid cartridge.

12. The apparatus of claim 11, further comprising a glass element having a thermal conductivity greater than a thermal conductivity of the ceramic chamber, the glass element at least partially surrounding an exterior of the ceramic chamber, the glass element thermally coupled with the heating element to transfer the thermal heat to the ceramic chamber.

13. The apparatus of claim 11, wherein the first end of the ceramic chamber is thermally coupled with the heating element to distribute the thermal energy through the ceramic chamber to convert to the gaseous form of the substance via partial or flash evaporation.

14. The apparatus of claim 11, wherein the processor is further configured to control operational settings of at least one of the heating element or the liquid cartridge based at least on one or more instructions received from a remote device.

* * * * *